(12) United States Patent
Holtkamp et al.

(10) Patent No.: US 8,462,203 B2
(45) Date of Patent: Jun. 11, 2013

(54) METHOD AND SYSTEM FOR MONITORING AND CONTROLLING A GLASS CONTAINER FORMING PROCESS

(75) Inventors: Mark Edwin Holtkamp, Groningen (NL); Teunis René Brummelman, Harkstede (NL)

(73) Assignee: Emhart Glass S.A., Cham (CH)

( * ) Notice: Subject to any disclaimer, the term of this patent is extended or adjusted under 35 U.S.C. 154(b) by 353 days.

(21) Appl. No.: 12/963,370

(22) Filed: Dec. 8, 2010

(65) Prior Publication Data
US 2011/0141264 A1   Jun. 16, 2011

(51) Int. Cl.
H04N 7/18     (2006.01)
G06K 9/00     (2006.01)

(52) U.S. Cl.
USPC ............................................. 348/86; 382/142

(58) Field of Classification Search
USPC ............................................. 348/86; 382/142
See application file for complete search history.

(56) References Cited

U.S. PATENT DOCUMENTS

| | | | |
|---|---|---|---|
| 3,968,368 | A | 7/1976 | Sager |
| 4,064,534 | A | 12/1977 | Chen et al. |
| 4,492,476 | A | 1/1985 | Miyazawa |
| 5,032,727 | A | 7/1991 | Cox et al. |
| 5,345,389 | A | 9/1994 | Calvin et al. |
| 5,583,337 | A | 12/1996 | Chan |
| 6,188,079 | B1 | 2/2001 | Juvinall et al. |
| 6,212,962 | B1 | 4/2001 | Lucas |
| 6,584,805 | B1 | 7/2003 | Burns |
| 7,054,710 | B2 | 5/2006 | Hartmann et al. |
| 2004/0262523 | A1 | 12/2004 | Bathelet et al. |
| 2006/0096319 | A1* | 5/2006 | Dalstra ................. 65/29.11 |
| 2007/0102628 | A1 | 5/2007 | Prasad |

FOREIGN PATENT DOCUMENTS

| | | |
|---|---|---|
| EP | 0 643 297 B1 | 12/2002 |
| EP | 1494012 A1 | 1/2005 |
| GB | 2149910 A | 6/1985 |
| JP | 20030083718 A | 3/2003 |
| WO | 0056673 A1 | 9/2000 |
| WO | 2004011935 A1 | 2/2004 |

OTHER PUBLICATIONS

Chan, Dr. John: "Automated Inspection and Container Monitoring at the Hot End." International Glass Review, Contract Communications, London, GB, Jan. 1, 1997, pp. 109-111, XP002991197. ISSN: 1359-4974 * the whole document *.
Micheletti, Roberto.: "Automatic Visual Inspection for Glass Production." ISMCR. Proceedings of the International Symposium on Measurement and Control in Robotics, XX, XX, Jan. 1, 1998, pp. 127-131, XP009069952 * abstract; section "3. Algorithm implementation" *.

* cited by examiner

Primary Examiner — David Czekaj
Assistant Examiner — Tsion B Owens
(74) Attorney, Agent, or Firm — Reinhart Boerner Van Deuren s.c.

(57) ABSTRACT

The present invention relates to a method and system for monitoring and controlling a glass container forming process. The radiation emitted by each hot glass container is measured with measurement unit immediately after the forming machine. The described method normalizes the measurement from glass container to glass container and thereby removes the effects of overall temperature variations between glass containers, changing ambient conditions, and other variations affecting the measurements, which provides a unique quality reference for each glass container. By reviewing this reference for each produced glass container, the quality of the produced containers can be improved.

20 Claims, 3 Drawing Sheets

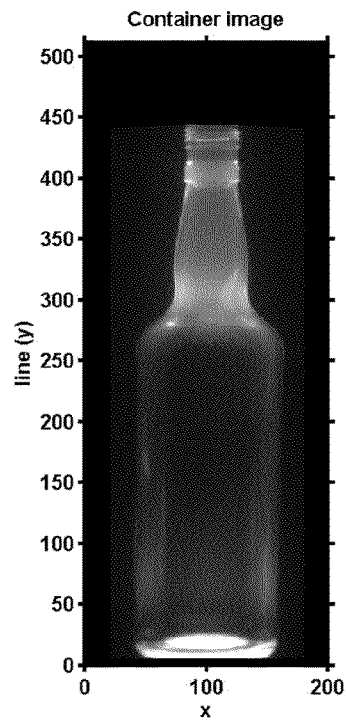
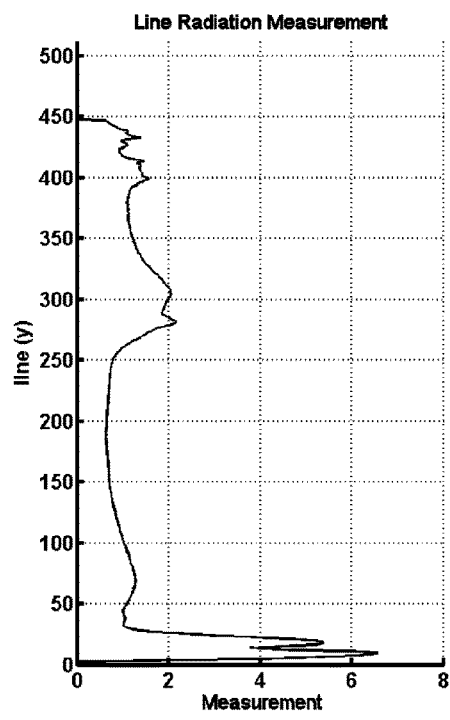
FIG. 2    FIG. 3
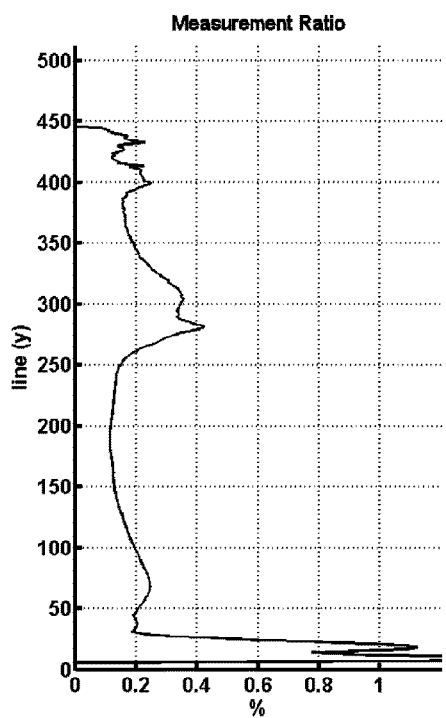
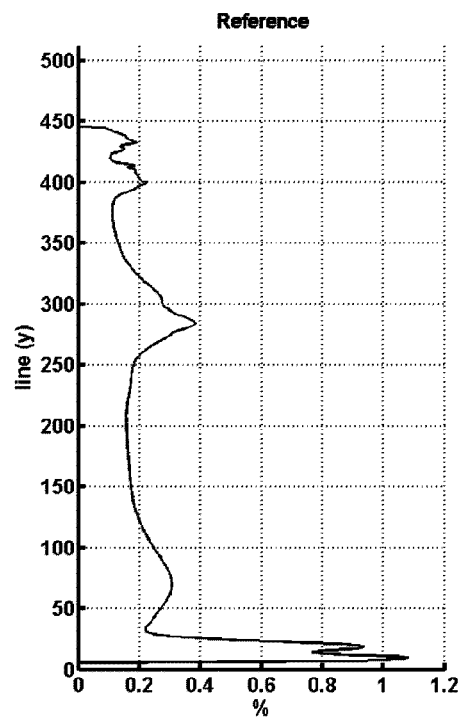
FIG. 4    FIG. 5

METHOD AND SYSTEM FOR MONITORING AND CONTROLLING A GLASS CONTAINER FORMING PROCESS

CROSS REFERENCE TO RELATED APPLICATIONS

This patent application claims priority benefit under 35 U.S.C. §119(a) from European Patent Application No. EP 09075545.5 filed in the European Patent Office on Dec. 10, 2009, the entirety of which patent application is hereby incorporated herein by reference.

BACKGROUND OF THE INVENTION

Field of the Invention

The present invention relates generally to a method and system for monitoring and controlling a glass container forming process.

The present invention relates to a method and system for monitoring and controlling a glass container forming process. The forming process is accomplished by a forming machine which may contain multiple independent sections, each section consisting of at least one forming station. The method comprises the steps of measuring radiation emitted by each hot glass container immediately after the forming machine. Based on these measurements, information and control signals may be generated to adjust the glass container forming process in order to improve the quality of the glass containers and by doing so reduce the number of bad glass containers produced.

A system of this type is disclosed in the European Patent EP 1525469 B1, to Dalstra, which describes a system for analyzing and monitoring a production process for glass products. The system is sensitive to radiation in the near infrared ("NIR") region solely and it measures the NIR radiation of hot glass products, determines the average radiation intensity for at least two measurement regions, compares this average intensity with a reference value, compares deviations between the measurement regions, and, based on this comparison, when necessary generates an error signal. In addition, a cooling curve is calculated and used as a reference to compensate for the difference in the amount of radiation of glass products due to different cooling times.

However, the system may generate error signals even when there is a change in the amount of radiation which is not brought about due to a change in the forming process, but is due instead to changes in the various conditions and parameters, such as, among others, the ambient temperature, ambient humidity, production speed, cooling air temperature, cooling air humidity, glass material composition, camera settings, smoke and dirt in the air, pollution of the optics, and container weight.

These conditions and parameters can drastically alter the measured radiation intensities depending on, for example, whether operating at day or night, different seasons, the production location, and/or the forming machine.

Consequently, an operator should always be present to monitor the measurement results and the generated error signals carefully, to check the conditions and parameters, and to adjust reference values in order to compensate for continuously changing conditions and parameters. From a practical point of view this is a very undesirable requirement, since labor costs are high and the forming process occurs in an extremely hot and noisy environment where labor conditions are quite unfavorable.

Another disadvantage of the system is that when starting the production of a glass container which has been produced earlier, the above mentioned conditions and parameters may have been changed, in which case the reference values and/or cooling curves used for the previous production may not be useful for the current production. In such a case, each time a new reference and/or a cooling curve is required, which will lengthen the start up time and is therefore not desirable.

It would be desirable to provide a method for monitoring and controlling a glass container forming process which is independent of the above mentioned conditions and parameters and with which it is possible to produce glass containers with a high and constant quality.

It would also be desirable to generate a unique reference which serves as a quality reference for the type of container produced, in order to produce glass containers at each forming station with the same quality depicted by this reference and to decrease the time necessary to start up the forming process. This unique reference may be stored and used to monitor and control the same forming machine or another forming machine producing the same particular glass container type at a different location.

It would also be beneficial to eliminate the requirement of having an operator monitoring the process constantly by instead controlling the forming machine automatically.

SUMMARY OF THE INVENTION

To achieve the above mentioned objects, the present invention relates to a method for monitoring and controlling a glass container forming process. The method measures infrared radiation emitted by hot glass containers immediately after the forming machine with a camera sensitive to the radiation emitted by the hot glass containers. The glass container image generated by the camera is arranged in a finite number of image lines, each image line having a finite number of pixels, and performs the following steps for each glass container measured from each forming station:

a. determining a total radiation measurement for each glass container by summing the digital values of all of the pixels in all of the image lines for such glass container;

b. determining a line radiation measurement for each image line for each glass container by summing the digital values of all of the pixels in such image line for such glass container; and c. determining a measurement-ratio curve for each glass container by dividing the line radiation measurements for each image line of such glass container by the total radiation measurement for such glass container.

The above mentioned problem of changing conditions and parameters is thereby compensated for by dividing the line radiation measurements by the total radiation measurement. This can be explained as follows. When, for example, the radiation of a hot glass container is partly absorbed by some smoke in the air, the line radiation measurement for the glass container get lower and the total measurement for the glass container gets lower. However, by dividing the line radiation measurements for the glass container by the total radiation measurement for the glass container, the line radiation measurements are in effect normalized to compensate for differences in total radiation measurement from glass container to glass container (the measurement-ratio curve is thus a normalized curve that will not be affected by differences in total radiation measurement from glass container to glass container). Obviously, this would not have been the case when, as in the prior art, absolute values of the radiation measurements for the glass containers are used without any normalizing of these values. (It should be noted that the measurement-ration curve is actually a dimensionless curve rather than being a dimensioned value.)

Glass containers originating from forming stations close to the measurement unit when compared to glass containers from forming stations further away from the measurement unit travel a shorter distance to the measurement unit which takes less time, and thus cool down less and consequently will have a higher temperature (and a correspondingly higher total radiation). In the prior art, a cooling curve was used to compensate for such different cooling times. However, this cooling curve is based upon absolute measured values, and was therefore sensitive to changes in above-mentioned conditions and parameters. According to the present invention, the measurement-ratio curve of the hot glass containers compensates for and normalizes the temperature of the glass container. When a glass container from a forming station located further away (which thus has a lower temperature) has the same glass distribution as a glass container from a forming station closer to the measurement unit (which thus has a higher temperature), the measurement-ratio curves from both glass containers will be the same instead of being markedly different as they would have been in prior art teachings.

The measurement-ratio curve of a hot glass container can further be compared with a reference curve. The reference curve is unique for each particular glass container type, and thus serves as a quality measure for each particular glass container type. In order to acquire this unique reference curve, a preferred embodiment of method may perform the following additional step:

d. determining a reference curve based upon a plurality of the measurement-ratio curves over a predetermined number of hot glass containers.

Averaging the measurement-ratio curves over a number of hot glass containers may include summing the measurement-ratio curves of a number of glass containers and dividing this sum by the number of glass containers. The measurement-ratio curves of the glass containers may be averaged over a period of time, from one or more selected stations, over a number of production cycles, or over just one production cycle.

One may obtain various reference curves with different forming machine settings, from which the one having the best performance, producing the best quality of glass containers, may be selected. This reference curve can be saved in order to be used when producing the same container type at a later time, either on the same forming machine or on a different forming machine. It can also be used to analyze and compare the current production performance with a past production. If desired, the reference curve can be continuously updated which may result in an even better quality being achieved for the same container.

Another preferred embodiment of method according to the present invention comprises the following step:

e. determining a relative difference curve for each hot glass container by subtracting the reference curve from the measurement-ratio curve of such hot glass container and dividing the result by the reference curve.

The relative difference curve easily shows how much and where the measurement-ratio curve of a glass container deviates from the reference curve. The relative difference curve can be displayed for each forming station in order to show the quality of the glass containers produced at the forming station. When the quality of a produced glass container is high, the relative difference curve will be close to zero. When the relative difference curves of all containers from all stations are close to zero, the quality of all containers produced by the forming machine will be high and substantially equal.

Another preferred embodiment of method according to the present invention comprises the following steps:

f. comparing the relative difference curve with a predetermined tolerance curve; and
g. generating an alarm signal if the relative difference curve exceeds the tolerance curve in at least one point.

By comparing the relative difference curve with a tolerance curve and generating an alarm signal if the difference exceeds the tolerance curve, one can easily determine whether the quality of glass containers produced by a forming station is acceptable or if it has degraded to such a degree that the container is of an inferior quality and therefore unacceptable.

The tolerance curve may be constant, tolerating the same amount of deviation for every location on said container. However, the values of the tolerance curve may also be dependant on the location on said container. By doing so, one is for instance able to allow less deviation from the reference curve for one or more areas of the container where the tolerances (e.g., the tolerance of the glass thickness) are critical. Furthermore, the tolerance values may be positive as well as negative.

The control unit controls the forming process of each forming station by a number of process parameters. In order to control the forming process automatically, another preferred embodiment of method according to the present invention comprises the following step:

h. sending the relative difference curve of each hot glass container to the control unit to automatically control the forming process.

By sending the relative difference curves of glass containers from each forming station to the control unit, the adjustment of the process may be performed automatically and shortly after the detection of a change or an error in the forming process. The adjustment will occur in such a manner that the relative difference curves substantially decreases to zero.

The measurement may be carried out at any wavelength at which a hot glass container emits radiation. Nevertheless, since radiation at wavelengths smaller than 3.0 microns from container glass is indicative of both the glass temperature and the glass thickness, a more accurate measurement may be obtained at wavelengths smaller than 3.0 microns, especially when analyzing relatively thicker glass containers. Therefore, a preferred embodiment method according to the present invention is that said measurement occurs for wavelengths of between 0.7 and 3.0 microns.

The present invention also relates to an analytical system for monitoring and controlling a glass container forming process. The system comprises at least one measurement unit to measure radiation emitted by each hot glass container immediately after the forming machine. The measurement unit may comprise a line-scan or area camera sensitive to the radiation emitted by the hot glass containers. The glass container image generated by the camera is arranged in a finite number of image lines, with each image line having a finite number of pixels. The processor unit provides calculations, comparisons, and communications with other units, wherein the processor unit is further programmed to carry out the following steps:

a. determining a total radiation measurement for each glass container by summing the digital values of all the pixels in all the image lines for such glass container;

b. determining a line radiation measurement for each image line for each glass container by summing the digital values of all the pixels in such image line for such glass container; and c. determining a measurement-ratio curve for each glass container by dividing the line radiation measurement for each image line of such glass container by the total radiation measurement for such glass container.

The processor unit is programmed such that it performs above mentioned operation in order to make the measured values of radiation independent not only of changes in parameters and conditions of the environment, process, and measuring equipment, but also independent of the forming station where a hot glass container originates from.

A further preferred embodiment of the analytical system according to the present invention is that the processor unit is further programmed to carry out the following step:

d. determining a reference curve by averaging the measurement-ratio curves over a predetermined number of the hot glass containers originating from all or a selected number of forming stations.

By summing the measurement-ratio curves of a number of hot glass containers and dividing the sum by the number of containers, an average measurement-ratio curve is acquired which is unique for a particular type of glass container. The average measurement-ratio curve may serve as a reference for the quality of glass containers of that particular type. It can also be utilized for another forming machine at a different location when producing the same type of glass container with the same quality requirements.

Another preferred embodiment of analytical system according to the present invention is that the processor unit is further programmed to carry out the following step:

e. determining a relative difference curve for each hot glass container by subtracting the reference curve from the measurement-ratio curve of each hot glass container and dividing the result by the reference curve.

By determining the relative difference curve, the quality of a hot glass container may be analyzed and the possible cause of a deficiency in the forming process may be indicated. By doing this, one can easily see how much and where the measurement-ratio curve of a hot glass container deviates from the reference curve. The relative difference curve can be displayed for each forming station in order to show the quality of the produced glass containers and to show the performance of the forming process. When the quality of a produced glass container is high, the relative difference curve will be zero or negligibly small.

Another preferred embodiment of analytical system according to the present invention is that the processor unit is further programmed to carry out the following step:

f. comparing the relative difference curve of each hot glass container with a predetermined tolerance curve;

g. generating an alarm signal if the relative difference curve exceeds the tolerance curve in at least one point.

By doing this, it can easily be determined whether the quality of the produced glass containers at a forming station is acceptable or not. The alarm signal may be used, for instance, to reject glass containers which have an unacceptable quality. The tolerance curve may be constant or it may be variable dependant on the location on the glass container.

Still another preferred embodiment of analytical system according to the present invention is that the processor unit is further programmed to carry out the following step:

h. sending the relative difference curve of each hot glass container to the forming control unit to automatically control the forming process.

The processor unit sends the relative difference curve of each glass container to the forming control unit, and the forming control unit, when necessary, adjusts one or more process parameters. This way, an automatic adjustment of process parameters is feasible shortly after the detection of an error or any detectable deficiency.

The measurement unit may be sensitive to any wavelength at which a hot glass container emits radiation. Nevertheless, since radiation at wavelengths smaller than 3.0 microns from container glass is indicative of both the glass temperature and the glass thickness, a more accurate measurement may be obtained at wavelengths smaller than 3.0 microns, especially when analyzing relatively thicker glass containers. Therefore, a preferred embodiment of analytical system according to the present invention is that the measurement unit is sensitive to wavelengths of between 0.7 and 3.0 microns. More specifically, the measurement unit uses a Short Wave Infrared ("SWIR") camera, for example a 512 or 1024 pixels line-scan or area SWIR camera.

DESCRIPTION OF THE DRAWINGS

These and other advantages of the present invention are best understood with reference to the drawings, in which:

FIG. 2 shows an image of a glass container;

FIG. 3 shows the line radiation measurements for the glass container shown in FIG. 2;

FIG. 4 shows a measurement-ratio curve for the glass container shown in FIG. 2;

FIG. 5 shows a reference curve for the glass container shown in FIG. 2;

DETAILED DESCRIPTION OF THE EXEMPLARY EMBODIMENT

Figure 1:
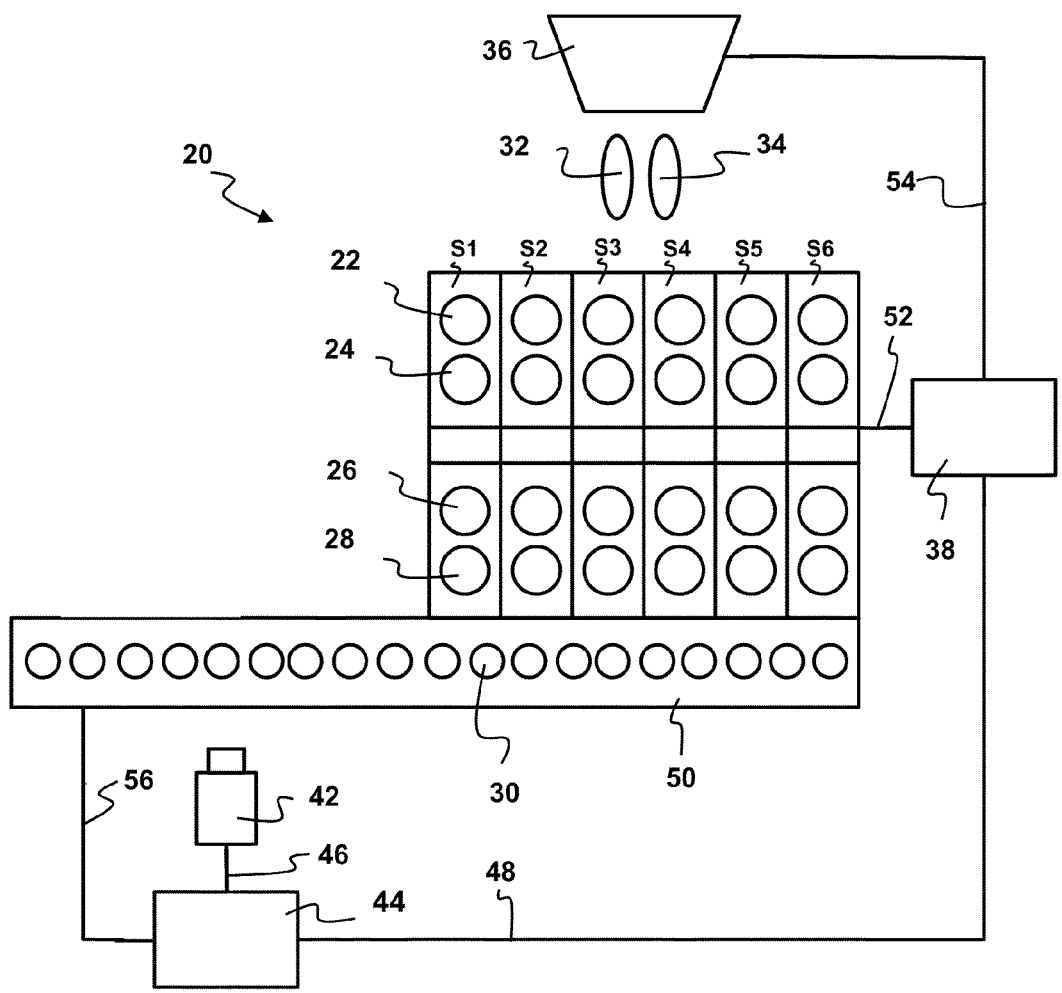
FIG. 1 shows a schematic view of a forming machine and an embodiment of the analytical system.

FIG. 1 shows an embodiment of the system where the glass container forming machine 20 contains six independent sections S1, S2, . . . S6, each of which contains two forming stations 22 and 24. In one production cycle, the forming machine 20 produces twelve glass containers 30. Two molten glass gobs 32 and 34 are formed at the same moment by the feeder unit 36 and are loaded into the so-called blank molds 22 and 24. Each section S1, S2, . . . S6 of the forming machine 20 in this embodiment contains two blank molds and 24 in which pre-containers or parisons are formed by pressing or blowing depending on the process type (press-blow or blow-blow). The formed parisons are transferred to the so-called blow molds 26 and 28 where the parisons are blown into the final shape of the glass containers 30. The mechanisms of the forming machine 20 and the feeder unit 36 are controlled by the control unit 38 through lines 52 and 54, respectively. The glass containers 30 are transported by a conveyor belt 50 through a measurement unit 42 which takes images of the hot glass containers 30 and sends these images to a processor unit 44 through a line 46. Although in this embodiment one measurement unit 42 is used, the number of measurement units 42 may be increased depending on the circumstances and the accuracy to be achieved. However, even with one measurement unit, the achieved accuracy is fairly high.

The measurement unit 42, an area camera in this embodiment, is preferably sensitive to Short Wave Infrared ("SWIR") radiation. The image taken by the camera of the hot glass container 30 shown in FIG. 2 may, for example, contain 512 image-lines, with each image-line for example containing 200 pixels.

The processor unit 44 determines for each glass container 30 the total radiation measurement by summing the digital values of all the pixels in the glass container image. The total radiation measurement of the glass container shown in FIG. 2 has a value of 553. Next, the processor unit 44 determines the line radiation measurements by summing for each image-line the digital values of all 200 pixels. The line radiation measurements belonging to the glass container image of FIG. 2 are shown in FIG. 3. Next, the processor unit 44, determines the measurement-ratio curve by dividing the line radiation measurements by the total radiation measurement, as shown hereunder:

$$I_{tot,s} = \Sigma I_{x,y,s} (x=1,2,\ldots 200, y=1,2,\ldots,512)$$

$$I_{y,s} = \Sigma I_{x,y,s} (x=1,2,\ldots 200)$$

$$I_{ratio,y,s} = (I_{y,s}/I_{tot,s})*100\%$$

Where:
- $I_{tot,s}$=the total radiation measurement value of a glass container image, originating from station s;
- $I_{x,y,s}$=the digital value of pixel x, y of the glass container image, originating from station s with y representing an image-line containing 200 x pixels, x=1 ... 200, y=1 .. . 512, s=1 ... 12;
- $I_{y,s}$=the line radiation measurement value for image-line (y) of a glass container image, originating from station s; and
- $I_{ratio,y,s}$=the measurement-ratio value for image-line y of a glass container image, originating from station s.

The measurement-ratio values are expressed in percentages for clarity. The measurement-ratio curve depicted in FIG. 4 belongs to the glass container shown in FIG. 2. The order in which these steps occur can be varied as long as the same results are achieved. One can easily see that, for example, an attenuation ● of the radiation received from the glass container 30 caused by an ambient parameter (for example smoke in the air) has no influence on the measurement-ratio curve:

$$I_{ration,y,s} = (\alpha I_{y,s}/\alpha I_{tot,s})*100\% = (I_{y,s}/I_{tot,s})*100\%$$

Next, the processor unit 44 determines a reference curve by averaging measurement-ratio curves from a number of glass containers 30 from all or certain selected forming stations. This reference curve is unique for the glass container type produced.

The values of the reference curve are derived as illustrated below:

$$I_{reference,y} = \left(\sum_{k=1}^{N} I_{ratio,y,k}\right)/N$$

Where:
- $I_{reference,y}$=the reference curve value for line (y); and
- N=the number of glass containers 30 taken into account.

Figure 6:
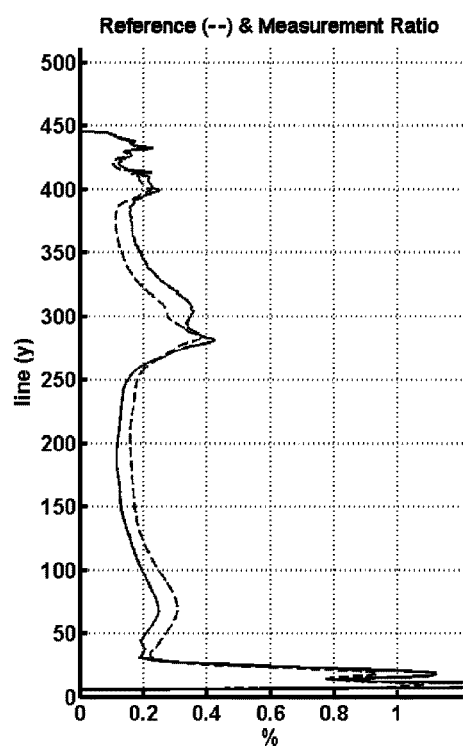
FIG. 6 shows a reference curve together with the measurement-ratio curve for the glass container shown in FIG. 2.

The reference curve may be stored and used later to decrease the time necessary to start up the production of the particular glass container 30 on the same or on another forming machine. The reference curve belonging to the glass container type in this example is shown in FIG. 5. In FIG. 6, the reference curve is shown together with the measurement-ratio curve of FIG. 4.

The processor unit 44 next determines the relative difference curve by subtracting the reference curve from the measurement-ratio curve and dividing the difference by the reference curve. This is illustrated hereunder:

$$\Delta I_{s,y} = ((I_{ratio,s} - I_{reference,y})/I_{reference,y})*100\%$$

Where:
- $\Delta I_{s,y}$=the relative difference value at line y of a glass container image originating from the station s.

Figure 7:
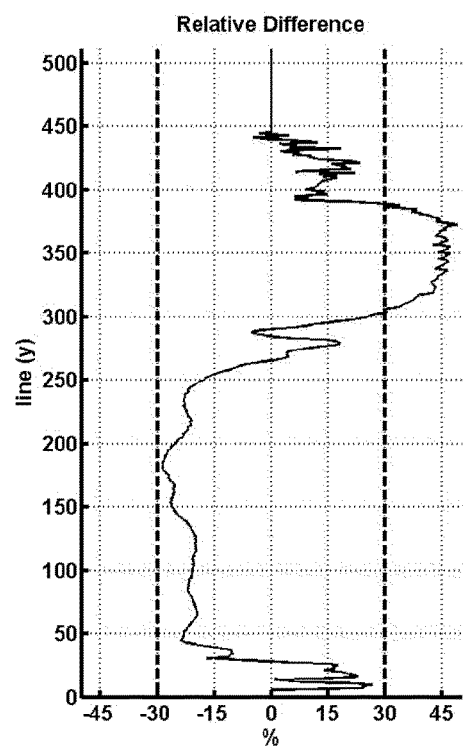
FIG. 7 shows a relative difference curve for the glass container shown in FIG. 2.

The relative difference curve shows how much and where the measurement-ratio curve of a glass container deviates from the reference curve. The processor unit 44 may display on a connected monitor (not shown) for each forming station the relative difference curve in order to show the quality of the glass containers produced at the forming station. In FIG. 7, the relative difference curve is shown for the glass container of FIG. 2 with the corresponding measurement-ratio curve shown in FIG. 4.

In this specific example the relative difference curve in FIG. 7 shows a positive deviation in the upper part of the glass container and a negative deviation in the lower part of the glass container, indicating too much glass in the upper part of the glass container and too little glass in the lower part of the glass container. The relative difference curve will be close to zero at every point for high quality glass containers.

Subsequently, the processor unit (44) compares the relative difference curve with predetermined tolerance curves and generates an alarm signal if a relative difference value exceeds the corresponding tolerance value. This is illustrated hereunder:

Alarm if:

$$\Delta I_{s,y} < I_{T-,y} \text{ or } \Delta I_{s,y} > I_{T+,y}$$

Where:
- $I_{T-,y}$=the negative tolerance value for line y; and
- $I_{T+,y}$=the positive tolerance value for line y.

The alarm signal may, for example, be used in order to reject glass containers which have an unacceptable quality on line 56 in FIG. 1. In FIG. 7 the negative tolerance values are set at −30% and the positive tolerance values are set at +30%. In FIG. 7 an alarm signal is generated because the relative difference values for line 300 through line 380 exceed the positive tolerance values.

In order to adjust the forming process automatically, the processor unit 44 may send the relative difference curve from each forming station to the control unit 38 over line 48. The control unit 38 adjusts the appropriate process parameters until the relative difference curve for each forming station is close to zero. This is then achieved without the need to have an operator monitoring the process continuously.

The processor unit 44 is synchronized with the forming machine 20 and with conveyor belt 50 in such a way that processor unit 44 knows from which forming station each glass container 30 originates.

The embodiment described above is intended solely to serve as an example, and in no way is intended to restrict the invention. A person skilled in the art given knowledge of this invention will rapidly be able to accomplish other embodiments. Therefore, any variation on the theme and methodology of accomplishing the same that are not described herein would be considered under the scope of the present invention.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A method for monitoring a glass container forming process wherein the forming process is accomplished by a forming machine which contains multiple independent sections each having at least one forming station at which glass containers are formed, comprising the steps of determining digital values proportional to the radiation emitted by hot glass containers immediately after the forming machine with a measurement unit sensitive to the radiation emitted by the hot glass containers, wherein the measurement unit generates a digital image of each hot glass container which is arranged in a finite number of image lines, each image line having a finite number of pixels, each pixel having a digital value, characterized in that the method further comprises the following steps for each glass container measured from each forming station:
    a. determining a total radiation measurement for each glass container by summing the digital values of all of the pixels in all of the image lines for such glass container;
    b. determining a line radiation measurement for each image line for each glass container by summing the digital values of all of the pixels in such image line for such glass container;
    c. determining a measurement-ratio curve for each glass container by dividing the line radiation measurements for each image line of such glass container by the total radiation measurement for such glass container;
    d. determining a reference curve based upon a plurality of the measurement-ratio curves over a predetermined number of the glass containers; and
    e. determining a relative difference curve for each glass container by subtracting the reference curve from the measurement-ratio curve for such glass container and dividing the result by the reference curve.

2. A method according to claim 1, wherein the method further comprises:
    f. comparing the relative difference curve of each hot glass container with a predetermined tolerance curve; and
    g. generating an alarm signal if the relative difference curve exceeds the tolerance curve in at least one point.

3. A method according to claim 1, wherein the forming machine is operated by a control unit, and wherein the method further comprises the following step:
    h. sending the relative difference curve of each hot glass container to the control unit to automatically control the forming process.

4. A method according to claim 1, wherein the measurement unit is sensitive to radiation wavelengths of between 0.7 and 3.0 microns.

5. A system for monitoring a glass container forming process, wherein the forming process is accomplished by a forming machine which is controlled by a control unit and which contains multiple independent sections each having at least one forming station at which glass containers are formed, comprising at least one measurement unit sensitive to the radiation emitted by the hot glass containers immediately after the forming machine, generating images of each hot glass container arranged in a finite number of image lines, each image line having a finite number of pixels, and a processor unit to provide calculations, comparisons and communications with other units, characterized in that the processor unit is further programmed to carry out the following steps for each glass container measured from each forming station:
    a. determining a total radiation measurement for each glass container by summing the digital values of all the pixels in all the image lines for such glass container;
    b. determining a line radiation measurement for each image line for each glass container by summing the digital values of all the pixels in such image line for such glass container;
    c. determining a measurement-ratio curve for each glass container by dividing the line radiation measurements for each image line of such glass container by the total radiation measurement for such glass container;
    d. determining a reference curve by averaging the measurement-ratio curves over a predetermined number of the containers originating from all or from a selected number of forming stations; and
    e. determining a relative difference curve for each hot glass container by subtracting the reference curve from the measurement-ratio curve of each hot glass container and dividing the result by the reference curve.

6. A system according to claim 5, wherein the processor unit is further programmed to carry out the following steps:
    f. comparing the relative difference curve of each hot glass container with a predetermined tolerance curve; and
    g. generating an alarm signal if the relative difference curve exceeds the tolerance curves in at least one point.

7. A system according to claim 5, wherein the relative difference curve of each hot glass container is sent to the control unit to automatically control the forming process.

8. A system according claim 5, wherein the processor unit is further programmed to carry out the following step:
    h. sending the relative difference curve of each hot glass container to the control unit to automatically control the forming process.

9. A system according to claim 5, wherein the measurement unit is sensitive to radiation wavelengths of between 0.7 and 3.0 microns.

10. A system according to claim 8, wherein the measurement unit comprises:
    a Short Wave Infrared (SWIR) camera.

11. A method of monitoring a glass container forming process using radiation emitted by hot glass containers formed in an I.S. machine, the method comprising:
    measuring radiation emitted by each hot glass container immediately after the glass container is formed and before it is cooled;
    determining, based on the measuring step, a line radiation measurement curve as well as a total radiation measurement for each hot glass container;
    determining a measurement-ratio curve for each container from each forming station by dividing the line radiation measurement curve by the total radiation measurement;
    determining a reference measurement-ratio curve based upon the measurement-ratio curves for a plurality of containers; and
    determining a relative difference curve for each hot glass container by subtracting the reference measurement-ratio curve from the measurement-ratio curve of each hot glass container and dividing the result by the reference measurement-ratio curve.

12. A method according to claim 11, wherein the method further comprises:
comparing the relative difference curve of each hot glass container with a predetermined tolerance curve.

13. A method according to claim 12, wherein the method further comprises:
generating an alarm signal if the relative difference curve exceeds the tolerance curve in at least one point.

14. A method according to claim 11, wherein the method further comprises:
using the relative difference curve of each hot glass container to automatically control the forming process.

15. A method according to claim 11, wherein the measuring radiation step is sensitive to radiation wavelengths of between 0.7 and 3.0 microns.

16. A system for monitoring a glass container forming process using radiation emitted by hot glass containers formed in an I.S. machine, the system comprising:
a measurement unit that measures radiation emitted by each hot glass container immediately after the glass container is formed and before it is cooled; and
a processor unit that determines, based on the measuring step, a line radiation measurement curve as well as a total radiation measurement for each hot glass container;
wherein the processor unit also determines a measurement-ratio curve for each container from each forming station by dividing the line radiation measurement curve by the total radiation measurement; and
wherein the processor unit also determines a reference measurement-ratio curve based upon the measurement-ratio curves for a plurality of containers; and
wherein the processor unit also determines a relative difference curve for each hot glass container by subtracting the reference measurement-ratio curve from the measurement-ratio curve of each hot glass container and dividing the result by the reference measurement-ratio curve.

17. A system according to claim 16, wherein the processor unit also compares the relative difference curve of each hot glass container with a predetermined tolerance curve.

18. A system according to claim 17, wherein the processor unit also generates an alarm signal if the relative difference curve exceeds the tolerance curve in at least one point.

19. A system according to claim 16, wherein the relative difference curve of each hot glass container is used to automatically control the forming process.

20. A system according to claim 16, wherein the measurement unit comprises:
a Short Wave Infrared (SWIR) camera.

* * * * *